March 13, 1956 M. MALANDRONE Plant Pat. 1,459
ROSE PLANT
Filed March 31, 1955
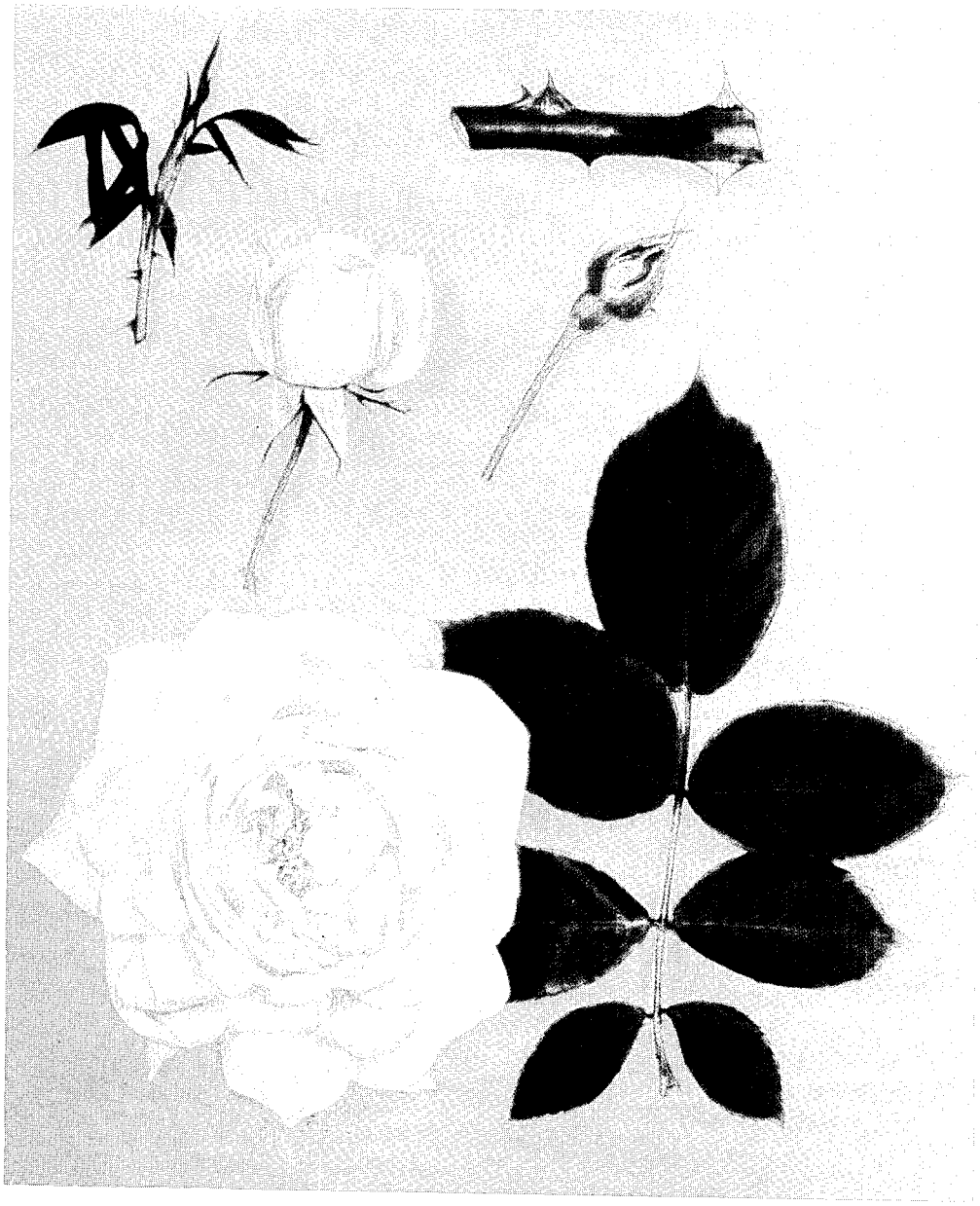
Inventor.
M. Malandrone
By: Robb & Robb
Attorneys.

United States Patent Office

Plant Pat. 1,459
Patented Mar. 13, 1956

1,459

ROSE PLANT

Michele Malandrone, Oakland, Calif., assignor to Jackson & Perkins Company, Newark, N. Y., a corporation of New York Application March 31, 1955, Serial No. 498,464

1 Claim. (Cl. 47—61)

The present invention relates to a new and distinct variety of rose plant of the climber class, which was originated by me by crossing the well-known variety "Mrs. Sam McGredy" (unpatented) with an unnamed and unpatented seedling of "Mrs. Sam McGredy" × another unnamed and unpatented seedling derived from crossing an unnamed and unpatented hybrid tea seedling with the variety "Captain Thomas" (Plant Patent No. 393).

The primary objective of this breeding was to obtain a free-producing, large-flowered climber of a distinctive Pink flower color. This objective was fully achieved, as evidenced by the fact that my new variety is particularly characterized as to novelty by the following outstanding features:

(1) A free-blooming habit which causes the flowers to be borne on the plant from the top thereof all the way to the ground;

(2) The free production of flowers intermittently throughout the growing season;

(3) The large size of the flowers; and (4) The distinctive Thulite pink color, lightly overcast with Cameo pink, of the blooms.

The foregoing characteristics and distinctions definitely differentiate my new variety from its parents, as well as from all other varieties of which I am aware, and asexual reproduction of the new variety by budding, as performed at Pleasanton, California, and also at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert Ridgway's Color Standards and Nomenclature:

Parentage: Seedling.

*Seed parent.*—"Mrs. Sam McGredy."

*Pollen parent.*—An unnamed seedling of "Mrs. Sam McGredy" × an unnamed seedling derived from crossing an unnamed hybrid tea seedling and "Captain Thomas."

Classification:

*Botanic.*—Climber.

*Commercial.*—Climber.

FLOWER (Observations made from specimens grown in a field at Newark, New York in the late morning and in the early part of the month of July.

Blooming habit: Recurrent—intermittent.

Bud:

*Size.*—Medium.

*Form.*—Ovoid; is not affected by wet or hot weather.

*Color.*—When sepals first divide—Carmine, Plate 1. When petals begin to unfurl—Eosine Pink, Plate 1. When half blown: inside of petals—Thulite Pink, Plate 26; reverse of petals—Thulite Pink, Plate 26, lightly overcast with Cameo Pink, Plate 26.

*Sepals.*—Branched; curl back when petals begin to unfurl. Color: inside—Pale Olivine, Plate 32; Outside—Jade Green, Plate 31.

*Calyx.*—Shape—pear. Size—long; small. Aspect—smooth. Odor when rubbed—none. Color—Biscay Green, Plate 17.

*Peduncle.* — Length — medium. Aspect — prickly. Strength—erect; slender. Color—Light Hellebore Green, Plate 17.

*Opening.*—Opens up well; is not affected by adverse weather conditions.

Bloom:

*Size.*—Large. Average size when fully expanded—from 4 inches to 4½ inches.

*Flowers borne.*—Singly and in irregular clusters.

*Stems.*—Medium length; normal strength.

*Form (when first open).*—Cupped. Permanence—flattens; outer petals curl back.

*Petalage.*—Double (full but open center). Number of petals under normal conditions—From 35 to 40.

*Color.*—Center of flower—Thulite Pink, Plate 26, lightly overcast with La France Pink, Plate 1. Outer petals—La France Pink, Plate 1, lightly overcast with Cameo Pink, Plate 26. Base of petals (aiglet)—Pale Lemon Yellow, Plate 4. Inside of petals—Thulite Pink, Plate 26, lightly overcast with Cameo Pink, Plate 26. Reverse of petals—Cameo Pink, Plate 26, lightly overcast with Cartridge Buff, Plate 30. General tonality from a distance—Thulite Pink, Plate 26, lightly overcast with Cameo Pink, Plate 26.

*Discoloration.*—General tonality at end of first day—Thulite Pink, Plate 26, lightly overcast with Cameo Pink, Plate 26. Second day—Thulite Pink, Plate 26, lightly overcast with Cameo Pink, Plate 26. Third day—La France Pink, Plate 1, lightly overcast with Cameo Pink, Plate 26.

Petals:

*Texture.*—Leathery; is not affected by wet or hot weather.

*Appearance.*—Inside—satiny; outside—shiny.

*Form.*—Oval.

*Arrangement.*—Informal (with "rags" in center).

*Petaloids in center.*—Few; small.

*Persistence.*—Drop off cleanly.

*Fragrance.*—Strong. Nature—Sweet tea fragrance.

*Lasting quality.*—On the plant—long; as cut flower—long.

GENITAL ORGANS

Stamens, anthers: Large; regularly arranged around styles.

*Color.*—Deep Chrome, Plate 3.

Stamens, filaments (threads): Long.

*Color.*—Lemon Yellow, Plate 4.

Pollen:

*Color.*—Pale Orange Yellow, Plate 3.

Styles: Columnar; uneven length; medium length; thin.

Stigmas:

*Color.*—Cartridge Buff, Plate 30.

Ovaries: All enclosed in calyx.

Hips: None.

Seeds: None.

PLANT

Form: Climber.
Growth: Vigorous; upright; branching.
Foliage: 5 to 7 leaflets.
*Size.*—Large.
*Quantity.*—Abundant.
*Color.*—New foliage: upper side—Dark Dull Yellow-Green, Plate 32, lightly overcast with Maroon, Plate 1; under side—Hay's Maroon, Plate 13. Old foliage: upper side—Deep Dull Yellow-Green, Plate 32; under side—Rainette Green, Plate 31.
*Shape.*—Oval pointed.
*Texture.*—Upper side—leathery; under side—smooth.
*Ribs and veins.*—Ordinary.
*Edge.*—Serrated (saw-toothed).
*Serration.*—Both double and single; small.
*Leaf stem.*—Color—Courge Green, Plate 17, lightly overcast with Carmine, Plate 1. Under side—prickles.
*Stipules.*—Medium length; smooth.
Wood:
*New wood.*—Color—Lettuce Green, Plate 5. Bark—smooth.

*Old wood.*—Color—Forest Green, Plate 17. Bark—smooth.
Thorns:
*Thorns.*—Quantity: on main stalks from base—ordinary; on laterals from stalk—ordinary. Form—broad base; medium length; hooked downward. Color (When young)—Indian Lake, Plate 26. Position—irregular.
*Prickles.*—Quantity: on main stalks—none; on laterals—none.
*Short needles.*—Quantity: on main stalks—none; on laterals—none.

I claim:

A new and distinct variety of rose plant of the climber class, substantially as herein shown and described, characterized particularly as to novelty by its free-blooming habit and consequent tendency to bear flowers from the top of the plant all the way to the ground, its free production of flowers intermittently throughout the growing season, the relatively large size of its flowers, and the distinctive Thulite pink general color tonality, lightly overcast with Cameo pink, of its flowers.

No references cited.